United States Patent [19]

Carruth

[11] Patent Number: Plant 7,580

[45] Date of Patent: Jul. 9, 1991

[54] HYBRID MINIATURE ROSE PLANT NAMED "WEKLIPS"

[76] Inventor: Thomas F. Carruth, 1182 E. Altadena Dr., Altadena, Calif. 91001

[21] Appl. No.: 496,817

[22] Filed: Mar. 20, 1990

[51] Int. Cl.[5] ..... A01H 5/00

[52] U.S. Cl. ..... Plt./7

[58] Field of Search ..... Plt. 7,9

*Primary Examiner*—James R. Feyrer

[57] ABSTRACT

A new hybrid miniature rose for garden decorating. The plant is of a dwarf, bushy, upright growth habit suitable for growing outdoor and may be distinguished from other presently available rose cultivars by the following combination of characteristics: abundant production of flowers, pointed buds, two-toned lavender coloration, and above average disease resistance and vigor, especially when compared to other lavender miniatures.

1 Drawing Sheet

BACKGROUND OF THE INVENTION

This invention relates to a new and distinct variety of hybrid miniature rose. The plant is of a dwarf, bushy, upright growth habit suitable for growing outdoor and may be cultivated for garden decoration. It was bred by Thomas F. Carruth in Canoga Park, Calif., and has as its seed parent, the rose known as "Shocking Blue" (U.S. Plant Pat. No. 3,846) and as its pollen parent, the rose known as "Helen Boehm". The varietal denomination of the new variety is "Weklips".

SUMMARY OF THE INVENTION

The new variety may be distinguished from other presently available commercial rose cultivars by the following combination of characteristics: pointed buds and well-formed flowers, two-toned lavender flower coloration essentially as described and illustrated herein, and above average disease resistance and vigor (especially when compared to other lavender miniature roses). Weklips may be propagated by cuttings, budding, grafting and tissue culture.

Asexual propagation of the new variety as performed in Kern County, Calif., shows that the foregoing and other distinguishing characteristics come true to perform and are established and transmitted through succeeding propagations.

The new rose may be distinguished from its seed parent, Shocking Blue, by the following combination of characteristics: whereas the seed parent is a hybrid floribunda, the new variety is a hybrid miniature. Whereas Shocking Blue bears flowers with a pronounced fragrance, the new cultivar has little perceivable fragrance in its flowers.

The new variety may be distinguished from its pollen parent, Helen Boehm, by the following combination of characteristics: whereas the pollen parent bears flowers of a light pink coloration, the new variety bears flowers of a two-toned lavender coloration essentially as described and illustrated herein. Whereas the new variety is very vigorous and abundant in its flowering, the pollen parent is significantly less vigorous under similar climatic conditions.

BRIEF DESCRIPTION OF THE ILLUSTRATION

The accompanying photograph illustrates the plant in color and shows the flowering thereof from bud to full bloom depicted in color as nearly correct as it is possible to make in an illustration of this character. Throughout this description color names and values are based upon the Colour Chart of The Royal Horticultural Society of London, England, except where common terms of color definition are employed.

DESCRIPTION OF THE NEW VARIETY

The following description pertains to roses of the new cultivar grown outdoor in November, 1989 in Kern County and in Upland, Calif. and is believed to apply to plants of the variety grown elsewhere in similar conditions of soil and climate.

FLOWER

The new variety bears its flowers singly, and in clusters of five or more per stem. Flowers are borne in regular rounded clusters on strong medium long stems for the class. Outdoor the plant blooms very abundantly and nearly continuously during the growing season. The flowers have little fragrance.

BUD

The peduncle is of short to average length for the class, of average to heavy caliper, and usually erect and stiff. It is moderately smooth with some stipitate glands and some hairs. Peduncle color is near to between Yellow-Green 144A and Green 137B.

Before the calyx breaks, the bud is of medium to large size for the class, medium length, and pointed to ovoid in shape. The surface of the bud bears some foliaceous appendages and some stipitate glands, usually with slender foliaceous parts extending beyond the tip of the bud equal to ½ or more of its length. Bud color is near to between Yellow-Green 147A and Green 137B.

The inner surface of the sepals is lined with fine wooly tometum: sepal margins are lined with some stipitate glands and many hairs.

As the first petals open, the bud is medium to large for the class, medium to long length, and moderately pointed to ovoid in form. The color of the outside surface of the newly opened petals is near to between Red-Purple 64A and Red 53A. The color of the inside surface of the newly opened petals is near to between Red-Purple 70C and Red-Purple 63D. The bud does open up well and is not prevented from opening by wet or dry weather.

BLOOM

When fully open, the bloom is moderately large for the class, ranging from 4 to 5.5 cm. in diameter. Petalage is double with 15 to 20 petals and 0 to 2 petaloids arranged regularly. When partially open, the bloom form is moderately cupped to high centered, and the petals are somewhat cupped to undulated with petal edges somewhat rolled outward. When fully open, the bloom form is somewhat flat to cupped, and the petals are moderately flat to undulated with petal edges somewhat rolled outward.

PETALS

The petals are of moderately heavy substance and of medium thickness, with inside surfaces slightly satiny to velvety and outside surfaces slightly shiny to satiny. The outside petals are broadly ovate to obovate in shape with apices somewhat rounded and sometimes slightly notched with one or more notches. The inside petals are less broadly ovate to obovate in shape with apices somewhat rounded to flat and sometimes slightly notched with one or more notches.

NEWLY OPENED FLOWER

The following describes the color values observed in flowers on a plant grown outdoor in Upland, Calif. in the month of November. Colors may be modified by being washed or shaded or tinted with other colors.

The outside surface of the outer petals is near to between Red-Purple 64B and Red-Purple 61B. The inside surface of the outer petals is near to between Red-Purple 70C and Red-Purple 63D.

The outside surface of the intermediate and inner petals is near to between Red-Purple 64C and Red-Purple 61C. The inside surface of the intermediate petals and inner petals is near to between Red-Purple 70C to D and Red-Purple 62C.

The general color effect of the newly opened flower is near to between Red-Purple 70C to D and Red-Purple 62C.

THREE DAY OLD FLOWER

The outside surface of the outer petals is near to between Red-Purple 67A to D and Red-Purple 63A. The inside surface of the outer petals is near to between Red-Purple 68C and Red-Purple 64A to D.

The outside surface of the inner petals is near to between Red-Purple 64C to D and Red-Purple 67A to D. The inside surface of the inner petals is near to between Red-Purple 70D and Red-Purple 63D.

The general color effect of the three day old flower is near to between Red-Purple 70D and Red-Purple 64D.

On the spent bloom, the petals usually drop off cleanly and are not particularly affected by wet or dry weather.

In November, blooms on the bush growing in the garden generally last from four to five or more days. Cut roses grown outdoor and kept at normal indoor living temperatures generally last five or more days.

MALE REPRODUCTIVE ORGANS

Stamens are average to many in number and are arranged regularly about the pistil. The filaments are of moderately short to medium length, most with anthers. The anthers are medium sized for the class and all open approximately at the same time. Anther color is near to Yellow-Orange 22B when immature and near to between Greyed-Orange 167B and Yellow-Orange 22C at maturity. Pollen is very abundant and near to Greyed-Yellow 162D in color.

FEMALE REPRODUCTIVE ORGANS

Pistils are somewhat few to average in number (approximately 35). The styles are somewhat even, moderately short to average length, average in caliper, and somewhat loosely bunched. Stigma color is near to between Yellow-White 158C and Yellow-Orange 19D. Ovaries are usually all enclosed in the calyx.

Hips on this variety when grown in Upland, Calif. are of short to average length, somewhat ovoid to globular in form, and near to Orange 24B in color when ripe. The hip surface is somewhat smooth with moderately thick fleshy walls. The sepals fall soon. Seeds are average to many in number (approximately 8 to 16), and moderately large in size for the class.

FOLIAGE

The compound leaves are usually comprised of compound three to five leaflets and are borne abundantly. The leaves are moderately large for the class, somewhat heavy in texture, and somewhat semi-glossy in finish. The leaflets are shaped moderately oval to ovate with somewhat acute to mucronate apices and very round bases. Their margins are usually simply dentate to irregular.

The upper surface of the mature leaf is near to between Yellow-Green 147A and Green 139A. The under surface of the mature leaf is near to between Green 138B and Greyed-Green 191B. The upper surface of the young leaf is near to between Yellow-Green 147A and Green 137B, sometimes lightly suffused with near Greyed-Purple 184B. The under surface of the young leaf is between Green 138B and Greyed-Green 191B, moderately suffused with near Greyed-Purple 184B.

The rachis is moderately heavy in caliper and somewhat rough to grooved with many hairs and stipitate glands. The under side of the rachis is moderately rough with some stipitate glands and prickles.

The stipules are somewhat medium in length with somewhat narrow width and medium to long straight points that usually turn out at an angle of less than 45 degrees.

The plant displays an above average degree of resistance to powdery mildew and rust as compared to other commercial varieties grown under comparable conditions in Upland, Calif.

GROWTH

The plant is of a dwarf, bushy, upright of medium height habit for the class with very full branching. It displays very vigorous growth and the canes are of moderately medium to heavy caliper for the class.

The major stems are near to between Green 137C and Yellow-Green 147B. They bear few large prickles which are medium length for the class. The large prickles are almost straight pointed slightly downward with a somewhat short to medium length somewhat broad base; prickle color is near Greyed-Orange 167D. The major stem bears few small prickles which are near Greyed-Orange 167D in color. There are no hairs.

The branches are near to between Green 137C and Yellow-Green 146B. They bear few large prickles which are medium length for the class, the large prickles are almost straight pointed slightly downward with a somewhat short to medium length somewhat broad base; prickle color is near Greyed-Orange 167B. The branches bear few small prickles which are near Greyed-Orange 167B in color. There are no hairs.

The new shoots are near to between Green 137B and Yellow-Green 146A often lightly suffused with near Greyed-Purple 184B. They bear few large prickles which are medium length for the class. The large prickles are almost straight pointed slightly downward with a somewhat short to medium length somewhat broad base; prickle color is near Greyed-Purple 184B. The shoots bear few small prickles which are near Greyed-Purple 184B in color. There are no hairs.

I claim:

1. A new and distinct variety of hybrid miniature rose plant substantially as shown and described, characterized by the plant's abundant production of flowers, pointed buds, flowers of two-toned lavender coloration, and above average disease resistance and vigor as compared to other lavender miniatures.

* * * * *

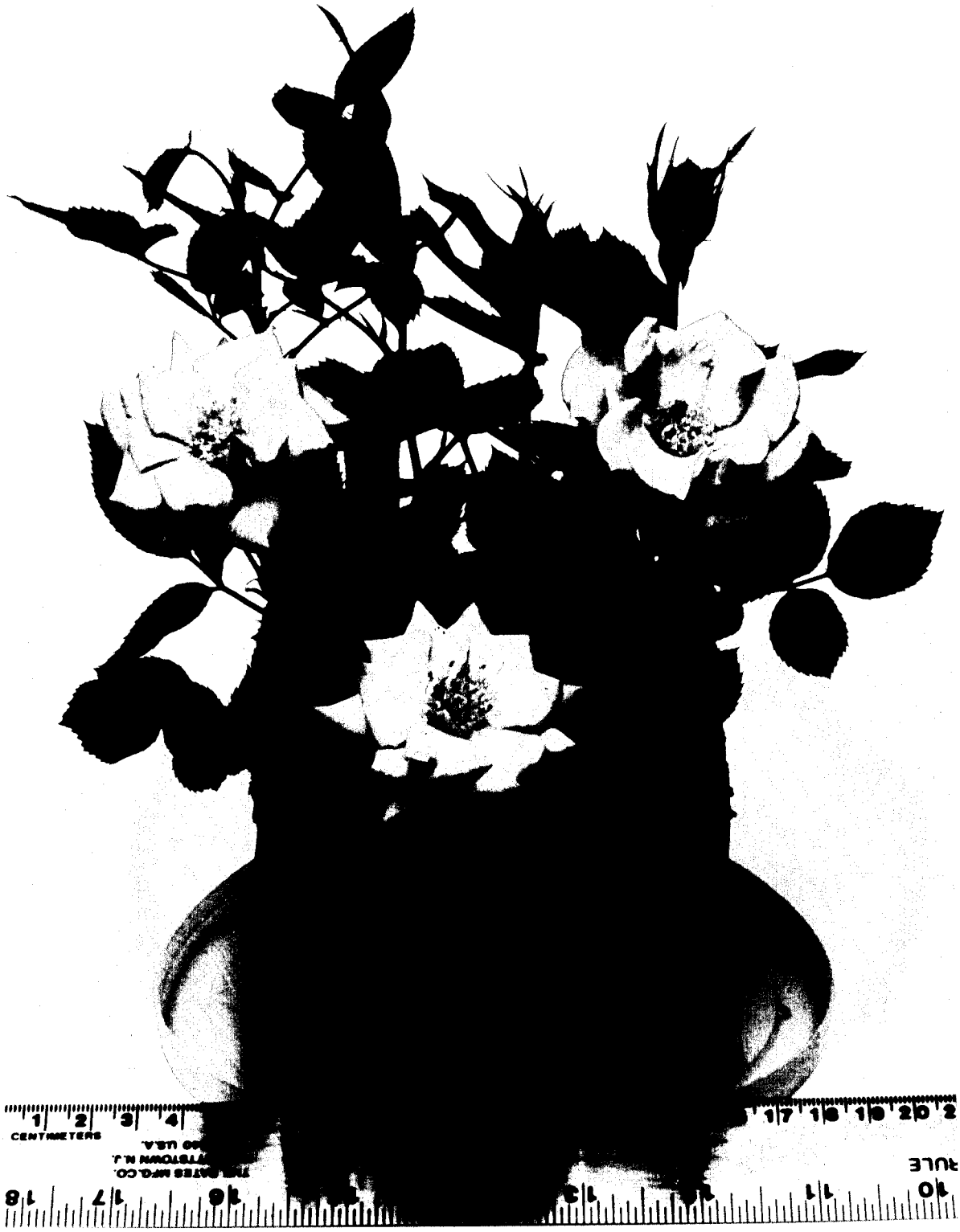
CENTIMETERS

UNITED STATES PATENT AND TRADEMARK OFFICE

CERTIFICATE OF CORRECTION

PATENT NO. : Plant 7,580

DATED : July 9, 1991

INVENTOR(S) : Thomas F. Carruth

It is certified that error appears in the above-identified patent and that said Letters Patent is hereby corrected as shown below:

On the title page:

Assignee, insert -- Weeks Wholesale Rose Grower, Inc., Upland, Calif. --.

Signed and Sealed this

Third Day of November, 1992

*Attest:*

*Attesting Officer*

DOUGLAS B. COMER

*Acting Commissioner of Patents and Trademarks*